(12) United States Patent
Harkins et al.

(10) Patent No.: US 6,638,364 B2
(45) Date of Patent: Oct. 28, 2003

(54) SYSTEM TO CLEAN AND DISINFECT CARPETS, FABRICS, AND HARD SURFACES USING ELECTROLYZED ALKALINE WATER PRODUCED FROM A SOLUTION OF NACL

(75) Inventors: Gene Harkins, Salt Lake City, UT (US); John M. Hopkins, Orem, UT (US)

(73) Assignee: Electric Aquagenics Unlimited, Lindon, UT (US)

( * ) Notice: Subject to any disclaimer, the term of this patent is extended or adjusted under 35 U.S.C. 154(b) by 0 days.

(21) Appl. No.: 09/947,121

(22) Filed: Sep. 5, 2001

(65) Prior Publication Data

US 2002/0112314 A1 Aug. 22, 2002

Related U.S. Application Data

(60) Provisional application No. 60/231,017, filed on Sep. 8, 2000.

(51) Int. Cl.$^7$ ................................................. A47L 9/02
(52) U.S. Cl. ........................ 134/21; 15/320; 15/321
(58) Field of Search .................. 15/320, 321; 422/292; 134/21

(56) References Cited

U.S. PATENT DOCUMENTS

| | | | | |
|---|---|---|---|---|
| 4,087,881 A | * | 5/1978 | Bates | 15/321 |
| 5,165,139 A | * | 11/1992 | Oxman | 15/321 |
| 5,815,869 A | * | 10/1998 | Hopkins | 15/321 |
| 5,839,155 A | * | 11/1998 | Berglund et al. | 15/321 |
| 6,132,572 A | * | 10/2000 | Kim | 204/253 |
| 6,357,454 B1 | * | 3/2002 | Yokota et al. | 134/167 C |

* cited by examiner

Primary Examiner—Theresa T. Snider
(74) Attorney, Agent, or Firm—Bracewell & Patterson, L.L.P.

(57) ABSTRACT

A system and method for cleaning and disinfecting soft surfaces such as carpets, fabrics and the like and for cleaning and disinfecting hard surfaces such as plaster, drywall, concrete, linoleum, counter tops, wood, metal, tile and the like is disclosed. The system and method uses electrolyzed alkaline water produced by an electrolysis process using a standard electrolyte solution of water and an electrolyte, wherein the electrolyte includes sodium chloride (NaCl) at a concentration between about 1% and 50%. In a preferred embodiment about a 20% concentration of sodium chloride is used. The electrolyzed alkaline water produced by this method is effective in cleaning and disinfecting both soft and hard surfaces.

10 Claims, 1 Drawing Sheet

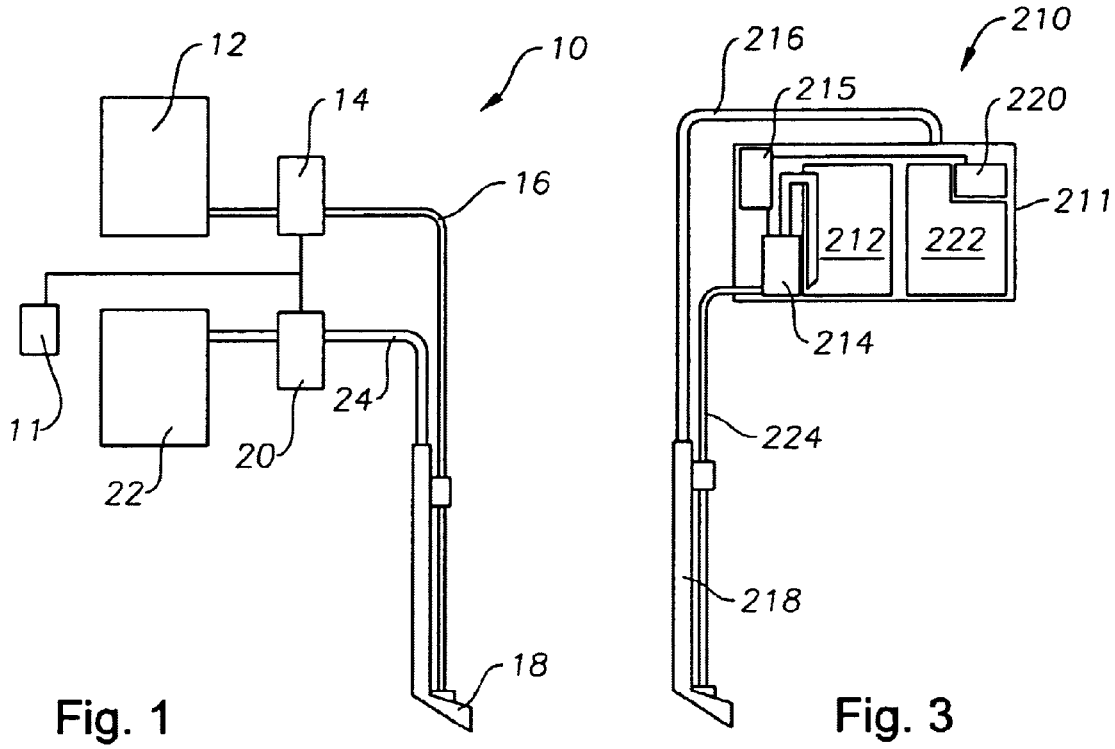
Fig. 1
Fig. 3
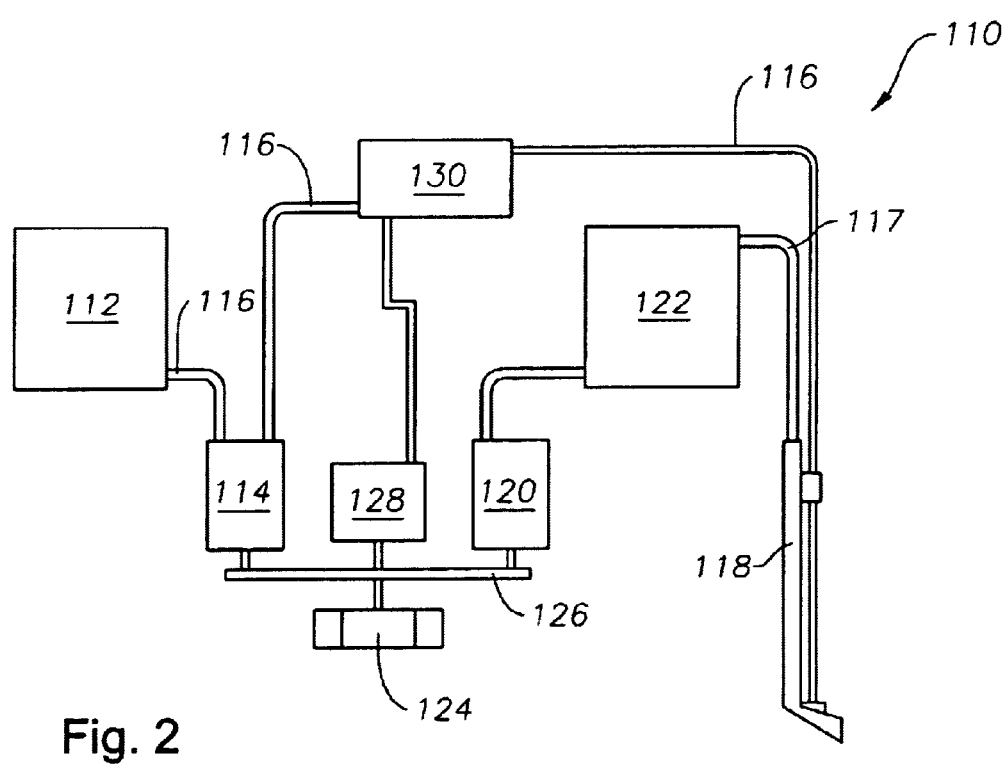
Fig. 2

SYSTEM TO CLEAN AND DISINFECT CARPETS, FABRICS, AND HARD SURFACES USING ELECTROLYZED ALKALINE WATER PRODUCED FROM A SOLUTION OF NACL

CROSS-REFERENCE TO RELATED APPLICATIONS

This application is a continuation of provisional patent application Ser. No. 60/231,017 filed Sep. 8, 2000.

THE FIELD OF THE INVENTION

This invention relates to cleaning generally, and more particularly to a system and method to clean and disinfect carpets, fabrics and hard surfaces by using electrolyzed alkaline water produced by an electrolysis process using the standard electrolyte solution of 20% sodium chloride (NaCl).

BACKGROUND OF INVENTION

Ever since carpets came into common use, people have wrestled with the difficulty of keeping them clean. Carpet, unlike other fabric in household use, is exposed to an enormous amount of foreign matter such as dirt, grass, leaves, sand, dust, mud, animal hair, and spilled food. The problem is compounded by both the permanent (e.g. wall-to-wall) installation of carpet and the length of fibers found in many carpets. Permanent (e.g. wall-to-wall) installation requires on-site cleaning. Bundles of yarns comprised of many fibers tend to capture or adhere to soiling, such as particulate matter. Conventional washing and cleaning processes remain ineffective.

"Hot-water extraction" methods have been developed to facilitate carpet cleaning. Hot water may actually include water; saturated, two-phase, steam and water; or superheated steam. The latter is not commonly relied upon, since it is typically hotter than the distortion temperature of synthetic fibers.

According to these methods, water is heated, pressurized, supplemented with chemical additives, and applied to carpet in order to dissolve or release soils and particulates and to suspend the resulting matter in the water (e.g. solvent, carrier, etc.). A "vacuum" system then extracts the dissolved soils, suspended particulates, and water out of the fibers. The water and air flows drawn by the vacuum system carry the entire mixture to a holding tank.

Most carpet and upholstery cleaning devices utilize a water-based cleaning solution that contains organic detergents. The solution is directed in a forceful stream onto the material to be cleaned. The temperature of the solution, the force of the directed stream, and the chemistry of the solution are all factors in the device's ability to clean effectively.

Hospital infections due to methicillin-resistant *Staphlococcus aaureus* (MRSA) have greatly increased since 1980. For prevention of hospital infection, thorough cleaning of the hospital environment is important. The hospital environment includes many soft fabric surfaces such as carpets. Additionally, hard tile floors, walls, counter tops, and the like must be cleaned and disinfected to prevent the spread of hospital infections. Chemical disinfectants have been usually used for this purpose. However, the use of chemical disinfectants creates the risk of generating resistant strains. Moreover, many chemicals used can be toxic to humans.

Electrolyzed oxidizing water (EO water) is useful for disinfecting and cleaning, and therefore can be used as an alternative to the detergent solutions for the cleaning of fabric, carpet, and hard surfaces. U.S. Pat. No. 5,815,869, to John M. Hopkins, discloses a cleaning system that utilizes a wand that both injects hot EO water at a high pressure and at a shallow angle, and simultaneously recovers the water by a strong vacuum. The EO water serves as a solvent, much of which leaves the wand in the form of microdroplets, to solublize dirt and greas from the fabric fibers. EO water is acidic with a pH of about 2.3 to 2.8. Electrolyzed alkaline water has a pH of about 11.2 to 11.6 and is produced with the same commercially available equipment that produces EO water. In the prior art, however, only the acidic EO water has been used with cleaning systems such as shown in U.S. Pat. No. 5,815,869.

BRIEF SUMMARY OF THE INVENTION

The present invention relates to a system and method of cleaning carpets, fabrics and hard surfaces with electrolyzed alkaline water produced from an electrolyte solution. According to one aspect of the invention, an electrolyte solution for producing electrolyzed alkaline water includes water and an electrolyte, wherein the electrolyte includes sodium chloride (NaCl).

In one presently preferred embodiment, an electrolyte solution is made by combining tap or other water with a concentration of about 1% to 50% sodium chloride. However, a concentration of 10% to 30% sodium chloride is more preferable. In certain embodiments a concentration of about 20% of sodium chloride is preferred. In other embodiments the NaCl may be used in a concentration of about 125 g/liter.

The electrolyte solution is converted into electrolyzed alkaline water along with EO water. Both have cleaning action, with the alkaline form superior for removing lipid based or organic stains. Both forms of electrolyzed water remove absorbed dirt and stains and have microbiocidal properties. Electrolyzed oxidizing water, which is mildly acidic, but very active, helps achieve a fresh, clean odor in the cleaning of carpet and hard surfaces. Electrolyzed oxidizing water having a pH of 2.8 or below, an oxidation-reduction potential of $1100^+$ millivolts (mV) or more and electrolyzed alkaline water having a pH of 11.2 to 11.6, an oxidation-reduction potential (ORP) of about −840 to −847 mV can be produced from tap water using a commercial water generator.

BRIEF DESCRIPTION OF THE DRAWINGS

In order that the manner in which the advantages and features of the invention are obtained, a more particular description of the invention summarized above will be rendered by reference to the appended drawings. Understanding that these drawings only provide selected embodiments of the invention and are not therefore to be considered limiting of the scope, the invention will be described and explained with additional specificity and detail through the use of the accompanying drawings in which:

FIG. 1 is a schematic diagram of a cleaning system in accordance with the present invention;

FIG. 2 is a schematic diagram of an alternate embodiment of the cleaning system of the present invention; and FIG. 3 is a schematic diagram of a portable cleaning system in accordance with the present invention.

DETAILED DESCRIPTION OF THE INVENTION

In one embodiment of the invention, an electrolyzing water generator is fed a combination of water and electrolyte that passes into channels containing electroplates which are either anodic (+) or cathodic (−). These plates are separated by a conductive diaphragm or special "membrane". Sodium chloride (NaCl) may be used to form the electrolyte solution necessary for current flow. In one embodiment of the invention, sodium chloride is used at concentrations of between 1% and 50%. More preferably, the sodium chloride is used at a concentration of about 10% to 30%. A concentration of about 20% sodium chloride is preferred in certain embodiments.

Pure water cannot be electrolyzed to any useful degree. Sodium and chloride ions ($Na^+Cl^-$) derived from the dissolution of NaCl migrate to opposite electrical poles. Thus when electrical energy is supplied to the machine, $Na^+$ flows in a net mass manner toward the cathode (−) and $Cl^-$ the anode (+). In general overview, water is decomposed (electrolyzed) owing to the high reactivity of $Na^+$ in the reaction where: $2Na^+ + 2H_2O = 2NaOH + H_2$. Since sodium ions are attracted to the cathode, the above reaction occurs in the cathodic channel to form a small amount of sodium hydroxide as water flows through the channel. The sodium hydroxide (NaOH) ionizes as $NaOH = Na^+ + OH^-$. The water from the cathode channel is called electrolyzed alkaline water which has a pH of 11.2 to 11.6 and oxidation reduction potential of about 840 to $847^-$ mV. Electrolyzed alkaline water is an excellent cleaning solution, particularly with lipid-based or organic stains.

In the anodic channel, where chloride ions ($Cl^-$) accumulate, electrons from $Cl^-$ are given up to the electron deficient anode and hence: $2Cl^- - 2e = Cl_2$. The chloride is soluble in water and reacts with water as $Cl_2 + H_2O = HOCl + H^+ = Cl^-$ forming a small amount of hydrochloric and hypochlorous acids as water flows through the channel. Hydrochloric acid is present at about 120 ppm and hydrochlorous acid at about 17 ppm. Other reactions occurring in the anodic channel include the formation of small amounts of hydrogen peroxide and ozone $H_2O_2$ and O3). The water from the anode channel is called electrolyzed oxidizing water or acid water. Owing to these chemical species, this solution is both acid and oxidative. This solution has an overall relative oxidation reduction potential (ORP) in the range of 1000 to $1200^+$ mV. Bacteria and viruses are readily killed by this solution, but it is safe in regard to humans and animals as accidental ingestion is not harmful.

From the above it is clear that water molecules are split in both channels, but with the chemistry divided by a conductive diaphragm or membrane, the net balance of chemical species is such that alkaline water (pH 11.2 to 11.6) is derived from the cathodic channel, and acid oxidation water (pH 2.8 to 2.3) from the anodic channel. This overall process is driven by the input of electrical energy and hence the term electrolysis.

Electrolyte solutions are typically added to feed water to increase the conductivity of the feed water when producing electrolyzed water in electrolyzing machines. The electrolyzed alkaline water produced by this method may be used to clean many soft surfaces and hard surfaces. Electrolyzed alkaline water is highly effective for removing organic stains such as oils and fats from carpets, fabrics and hard surfaces and has microbiocidal properties.

It is thought by some scientists that electrolyzed water is restructured such that the cluster size (number of water molecules that are weak-hydrogen-bonded to form molecular aggregates) is smaller than for ordinary water. Smaller cluster size would, predictably, reduce viscosity and increase the solvent qualities of the water. Addition of inorganic ions can alter the solvent capabilities and perhaps slightly restructure water. Inorganic ions are surrounded by a shell of water molecules, the size of which varies with the type of ion. When such modified water is heated and injected into a fabric at high speed by the wand of a commercial carpet cleaning apparatus, it quickly and effective cleanses carpet and fabric fibers. Extraction is further enhanced by formation of microdroplets of water which are generated by the spray wand aperture. A suitable cleaning apparatus for this purpose is disclosed in U.S. Pat. No. 5,815,869, the entire disclosure of which is included herein by reference.

In certain presently preferred embodiments of the invention, filtered water is used as feed water. However, other types of water can be used for feed water, including tap water, deionized water, and distilled water, or a combination of the aforesaid feed waters.

Referring to FIG. 1, a cleaning system for use with electrolyzed alkaline water is designated 10. The cleaning system includes a storage tank 12 for storing electrolyzed alkaline water. The electrolyzed alkaline water is drawn from the storage tank 12 by a pump 14. The electrolyzed alkaline water travels through a hose 16 and into a wand 18. The water exits the wand 18 under pressure and is sprayed on a surface to be cleaned and disinfected. The surface may be a soft or hard surface. Soft surfaces may include carpets, upholstery, leather, fabrics and the like. Hard surfaces may include tile, plaster, drywall, concrete, linoleum, counter tops, wood, metal and the like.

As the water exits the wand, suction from a vacuum 20 simultaneously draws the water into a second hose 24. The water travels through the second hose 24 to a waste water tank 22. A power supply 11 provides power to the pump 14 and the vacuum 20. The electrolyzed alkaline water both cleans the surface by removing dirt and oil and also disinfects the surface.

Referring to FIG. 2, an alternate embodiment of a cleaning system is designated 110. The cleaning system 110 includes a storage tank 112 for storing electrolyzed alkaline water. The electrolyzed alkaline water is drawn from the storage tank 112 by a pump 114. The electrolyzed alkaline water travels through a hose 116 to a heater 130 where the water is heated to an optimal temperature for cleaning and disinfecting. The water exits the heater 130 through a hose 116 and travels to a wand 118. The water exits the wand 118 under pressure and is sprayed on a surface to be cleaned and disinfected. The surface may be a soft or hard surface. Soft surfaces may include carpets, upholstery, leather, fabrics and the like. Hard surfaces may include tile, plaster, drywall, concrete, linoleum, counter tops, wood, metal, and the like.

As the water exits the wand, suction is applied by a vacuum 120. The water travels through another hose 117 to the waste water tank 122. The electrolyzed alkaline water both cleans the surface by removing dirt and oil and also disinfects the surface.

The cleaning system 110 may be mounted to a truck or other vehicle to allow the cleaning system 110 to be taken to many locations. A power source 124 such as the motor from the truck or a gas or electric motor turns a belt 126. The belt 126 powers the vacuum 120, the pump 114, and a generator 128. The generator 128 creates a power supply for running heater 130. The heater 130 heats the electrolyzed alkaline water for better cleaning and disinfecting.

Referring to FIG. 3, a portable or handheld cleaning system is designated 210. The portable cleaning system 210 has a compact body 211 in which the parts of the cleaning system 210 are located. The cleaning system 210 may be mountable on wheels or rollers for ease of mobility. The cleaning system 210 may also be configured with straps allowing a user to carry the cleaning system like a backpack.

A storage tank 212 for storing electrolyzed alkaline water, a pump 214, a power supply 215, a vacuum 220, and a waste tank 222 are located within the body 211 of the cleaning system 210. The power supply provides power to the pump 214 and the vacuum 220.

The electrolyzed alkaline water is drawn from the storage tank 212 by the pump 214. The electrolyzed alkaline water travels through a hose 216 and into a wand 218. The water exits the wand 218 under pressure and is sprayed on a surface to be cleaned and disinfected. The surface may be a soft or hard surface. Soft surfaces may include carpets, upholstery, leather, fabrics and the like. Hard surfaces may include tile, plaster, drywall, concrete, linoleum, counter tops, wood, metal and the like.

As the water exits the wand 218, suction from the vacuum simultaneously draws the water into a second hose 224. The water travels through the second hose 224 to the waste water 222. The electrolyzed alkaline water both cleans the surface by removing dirt and oil and also disinfects the surface.

I claim:

1. A cleaning system for cleaning and disinfecting carpets, fabrics or hard surfaces, comprising:
    a cleaning solution tank having an outlet and containing a cleaning solution that includes electrolyzed alkaline water;
    a cleaning wand connected with the outlet for applying the cleaning solution from the cleaning solution tank to a surface;
    a waste fluid tank in communication with the cleaning wand; and
    a vacuum pump that communicates with the waste fluid tank for creating a vacuum in the waste fluid tank to collect in the waste fluid tank cleaning solution that has been applied to the surface.

2. The cleaning system of claim 1, further comprising a pump communicating between the outlet and the cleaning wand for pumping cleaning solution from the cleaning solution tank to the cleaning wand.

3. The cleaning system of claim 1, further comprising a heater located between the outlet and the cleaning wand for heating the cleaning solution flowing from the cleaning solution tank.

4. The cleaning system of claim 1, wherein the electrolyzed alkaline water has a pH greater than 11.2.

5. A cleaning system for cleaning and disinfecting carpets, fabrics or hard surfaces, comprising:
    a cleaning solution tank having an outlet and containing a cleaning solution that includes electrolyzed alkaline water;
    a cleaning wand connected with the outlet for applying the cleaning solution from the cleaning solution tank to a surface;
    a pump communicating between the outlet and the cleaning wand for pumping cleaning solution from the cleaning solution tank to the cleaning wand;
    a heater located between the outlet and the cleaning wand for heating the cleaning solution flowing from the cleaning solution tank;
    a waste fluid tank in communication with the cleaning wand; and
    a vacuum pump that communicates with the waste fluid tank for creating a vacuum in the waste fluid tank to collect in the waste fluid tank cleaning solution that has been applied to the surface.

6. The cleaning system of claim 5, wherein the electrolyzed alkaline water has a pH of at least 11.2.

7. A method of cleaning carpets, fabrics and hard surfaces, comprising:
    (a) placing a cleaning solution that includes electrolyzed alkaline water in a cleaning solution tank;
    (b) discharging the cleaning solution from the cleaning solution tank out a cleaning wand onto a surface to be cleaned; and
    (c) creating a vacuum in a waste fluid tank and drawing into the waste fluid tank cleaning solution that has been applied to the surface.

8. The method of claim 7, wherein step (b) comprises pumping the cleaning solution from the cleaning solution tank to the wand.

9. The method of claim 7, wherein step (b) further comprises heating the cleaning solution as it flows from the cleaning solution tank to the wand.

10. The method of claim 7, wherein step (a) comprises providing the electrolyzed alkaline water with a pH greater than 11.2.

\* \* \* \* \*